United States Patent [19]

Bradley et al.

[11] Patent Number: 4,720,561

[45] Date of Patent: Jan. 19, 1988

[54] PREPARATION OF METAL ALKYLS

[75] Inventors: Donald C. Bradley, Middlesex; Halina Chudzynska; Marc M. Faktor, both of London, all of England

[73] Assignee: The Secretary of State for Defence in Her Britannic Majesty's Government of the United Kingdom of Great Britain and Northern Ireland, London, England

[21] Appl. No.: 817,848

[22] PCT Filed: Mar. 26, 1985

[86] PCT No.: PCT/GB85/00116

§ 371 Date: Nov. 25, 1985

§ 102(e) Date: Nov. 25, 1985

[87] PCT Pub. No.: WO85/04405

PCT Pub. Date: Oct. 10, 1985

[30] Foreign Application Priority Data

Mar. 26, 1984 [GB] United Kingdom ............. 8407808
Dec. 7, 1984 [GB] United Kingdom ............. 8430979

[51] Int. Cl.$^4$ .................... C07F 5/00; C07F 5/06
[52] U.S. Cl. ........................................ 556/1; 556/18; 556/174
[58] Field of Search .................... 556/1, 18, 174

[56] References Cited

U.S. PATENT DOCUMENTS

| | | | |
|---|---|---|---|
| 2,971,017 | 2/1961 | Fischer et al. | 556/1 |
| 3,048,612 | 8/1962 | Walde | 556/1 X |
| 3,211,707 | 10/1965 | Schulthess | 556/174 X |
| 3,308,143 | 3/1967 | Poe et al. | 556/174 X |
| 3,310,574 | 3/1967 | Todt et al. | 556/1 |
| 3,318,931 | 5/1967 | Dötzer et al. | 556/1 |
| 3,367,989 | 2/1968 | Scoggins et al. | 556/174 X |
| 3,607,257 | 9/1971 | Johnson | 556/1 X |
| 3,657,298 | 4/1972 | King et al. | 556/18 X |
| 4,604,473 | 8/1986 | Hamilton et al. | 556/1 |

FOREIGN PATENT DOCUMENTS

| | | |
|---|---|---|
| 2123422 | 4/1974 | United Kingdom. |
| 2123423 | 4/1974 | United Kingdom. |
| 2125795 | 7/1974 | United Kingdom. |
| 466238 | 1/1975 | U.S.S.R. ............. 556/1 |
| 388563 | 3/1976 | U.S.S.R. ............. 556/1 |

OTHER PUBLICATIONS

Durkin et al, Inorg. Chem. vol. 11 (5) pp. 1054–1059 (1972).
Chemical Abstracts 77 74383p (1972).
Chemical Abstracts 77 19712v (1972).

Primary Examiner—Helen M. S. Sneed
Attorney, Agent, or Firm—Stevens, Davis, Miller & Mosher

[57] ABSTRACT

A method of preparing a metal alkyl of formula $(R_3M)_x$ where $R_3$ represents three alkyl groups R which may be the same or different, M represents a Group III metallic element and x is 1 or 2, which method comprises (a) forming a trialkyl adduct of formula $(R_3M)_y.L$ wherein L represents an aryl-containing Group V, preferably phosphorus, donor ligand provided by an organic Lewis base which is stable at 20° C., and wherein Y is an integer equal to the number of Group V atoms presents in the ligand, and (b) heating the adduct to provide thermal dissociation thereof thereby releasing the alkyl as a gaseous product.

13 Claims, 2 Drawing Figures

PREPARATION OF METAL ALKYLS

The present invention relates to the preparation of metal alkyls useful in the preparation of compound semiconductor materials.

Compound semiconductor materials, eg materials such as gallium arsenide, indium phosphide, gallium phosphide and cadmium mercury telluride, are well known materials having uses in the electronics industry in such applications as microwave oscillators, semiconductor light emitting diodes and lasers, and infrared detectors.

Such materials have been made in the past by forming, usually on a substrate crystal, one or more active layers, by the method of vapour phase epitaxy (VPE).

It has been known for some time that compound semiconductors of the form MQ where M is a Group III element and Q is a Group V element may be produced by VPE by reacting a trialkyl of the element M with a gaseous compound, eg a hydride, of the Group V element Q. This method is a suitable method of preparing gallium arsenide from $Ga(CH_3)_3$ and $AsH_3$ for example.

Consequently, metal alkyls, in particular Group III trialkyls, such as trimethyl gallium and trimethyl indium have become important in the production of semiconductor materials.

However, metal alkyls such as trimethyl gallium and trimethyl indium are exceedingly hazardous by virtue of their volatile pyrophoric nature, and explosive hydrolytic reactivity.

Special containers are required for trimethyl gallium and trimethyl indium and these are very expensive to provide.

In the article by H Renz and J Weidlein in Electronics Letters, Mar. 13, 1980, Vol 16 No 6, there is described the formation of an adduct of trimethyl indium with the Lewis base $P(CH_3)_3$. The adduct so produced is a solid at room temperature, which is not hazardous and may be purified by zone refining. However, it is difficult to separate the trimethyl indium from the adduct described in that reference.

The purpose of the present invention is to provide a method of forming a metal alkyl from an adduct thereof by providing an adduct which is stable at room temperature and, when required is easily separable into its components above a relatively low thermal decomposition (dissociation) temperature.

According to the first aspect of the present invention there is provided a method of preparing a Group III metal alkyl which comprises comprises (a) forming an adduct of the aalkyl, the adduct having the formula $(R_3M)_y.L$ wherein $R_3$ represents three alkyl groups R which may be the same or different, M represents a Group III metallic element, L represents an aryl-containing Group V donor ligand provided by an organic Lewis base which is stable at 20° C. and wherein y is an integer equal to the number of Group V donor atoms present in the ligand, and (b) heating the adduct to provide thermal dissociation thereof thereby releasing the metal alkyl as a gaseous product. L is preferably an aryl-containing phosphorus donor ligand.

The present method is especially suitable for the preparation of lower alkyls of Group III metals, particularly hexamethyl dialuminium, trimethyl gallium and trimethyl indium.

Suitable Lewis bases for providing the ligand L are aryl-containing Group V Lewis bases, especially those in which the or each Group V donor atom present in the base is trivalent and is bonded directly to at least one adjacent aryl groups. The main advantages of employing an aryl rather than an alkyl Lewis base are that i. the basicity of the Lewis base is reduced, so that the adduct produced from it has a lower dissociation temperature, and ii. the volatility of the Lewis base is generally lower.

As a result of these two advantages, the adducts formed by the method of the present invention are easily dissociated at relatively low temperatures producing a gaseous alkyl product which contains only very low concentrations of Lewis base contaminant.

Aryl-containing Group V Lewis bases which have been found to have acceptably low volatilities for the purpose of the present invention are those having a melting point in the range 50° C. to 200° C. Furthermore, it has been found that those Lewis bases which give rise to adducts of formula $(R_3M)_y.L$ having a heat of formation of between 5 and 15 kcal mol$^{-1}$, especially from 6 to 12 kcal mol$^{-1}$, are preferred. Adducts having a heat of formation of less than about 5 kcal mol$^{-1}$ will tend to dissociate at room temperature (15°–20° C.) and thus be unsuitable for the present method, whereas adducts having a heat of formation of more than 12 kcal mol$^{-1}$ and particularly more than 15 kcal mol$^{-1}$ generally require unacceptable high dissociation temperatures which can lead to high levels of Lewis base contamination in the gaseous alkyl product.

Both the ligand L and the organic Lewis base from which it is derived are preferably of general formula I

and are most preferably of general formula II

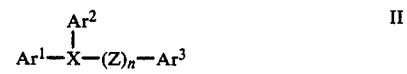

wherein
$Ar^1$, $Ar^2$ and $Ar^3$ are the same or different and are aryl groups,
X is a Group V atom,
Y is an aryl or aryl-containing group,
Z is

wherein D is an aromatic or aliphatic group and $Ar^4$ is an aryl group, and n is an integer from 1 to 5. Preferably X is phosphorus.

Each of the groups $Ar^1$, $Ar^2$ and (in Formula II) $Ar^3$ and $Ar^4$ may be selected from phenyl, substituted phenyl (eg o-, p-, or m-tolyl $C_6H_4CH_3$, or mesityl $C_6H_2(CH_3)_3$), p-diphenyl or naphthyl. Preferably, the groups $Ar^1$, $Ar^2$, $Ar^3$ and $Ar^4$ are phenyl.

D is preferably an aliphatic chain $(CH_2)_m$ where m is an integer from 1 to 12, most preferably from 2 to 4, and n is preferably from 1 to 3.

Examples of monodentate ligands L of general formula I are triphenylphosphine, tris-p-toylphosphine, trimesitylphosphine, tris-p-biphenylphosphine and tri-naphthylphosphine. Examples of bi- and poly-dentate ligands L of general formula II are DIPHOS($Ph_2PCH_2CH_2PPh_2$), TRIPHOS($Ph_2PCH_2CH_2P(Ph)CH_2CH_2PPh_2$) and TETRAPHOS-1($Ph_2PCH_2CH_2P(Ph)CH_2CH_2P(Ph)CH_2CH_2PPh_2$) (Ph=phenyl).

One particular advantage of employing bi- and especially poly-dentate Lewis bases of general formula II over mono-dentate Lewis bases of general formula I are that the former are found to be more likely to form adducts of formula $(R_3M)_y.L$ whose thermal dissociation temperature is below the melting point of the base The rate of liberation of alkyl from a solid base/adduct mixture is solely dependent on temperature and is virtually unaffected by the changing concentrations of the adduct and the Lewis base dissociation product as dissociation proceeds. The present inventors have found that a further advantage of employing Lewis bases of general formula I, and especially when employing Lewis bases of general formula II, when X is phosphorus is that they do not in general readily form adducts with Group II metals. Group II metals present even in trace amounts can interfere with the growth of Group III/Group V compound semiconductor layers by VPE and can act as unwanted dopants in these layers. The use of these aryl-containing phosphorus Lewis bases in the present method can therefore additionally provide a method of purifying Group III metal alkyls because the adduct $(R_3M)_y.L$ produced by the method is generally free of Group II metal impurities.

The adduct $(R_3M)_y.L$ is preferably prepared by producing a precursor adduct of formula $R_3M.E$ where E represents an ether, and causing a substitution reaction between the precursor adduct $R_3M.E$ and the Group V donor ligand L. Although L may be weaker as a Lewis base than E, the equilibrium of the substitution reaction may be disturbed, so as to produce the desired $(R_3M)_y.L$ adduct, by distilling off the volatile ether E.

For example, E may be diethyl ether and may be displaced by $PAr_3$, particularly triphenylphosphine etc as specified above, or by DIPHOS, TRIPHOS, or TETRAPHOS. As an example a heat of reaction of approximately 20 kcal $mol^{-1}$ (84 kJ $mol^{-1}$) is produced in the formation of $(CH_3)_3Ga.(C_2H_5)_2O$, whereas a heat of reaction of only approximately 6 kcal $mol^{-1}$ (25 kJ $mol^{-1}$) is produced in the formation of $(CH_3)_3Ga.PPh_3$ containing the weaker Lewis base $PPh_3$. Adducts having a heat of reaction of less than about 5 kcal $mol^{-1}$ (21 kJ $mol^{-1}$) in their formation will tend to dissociate at room temperature and thus be unsuitable as the adduct.

The precursor adduct of formula $R_3M.E$ may be prepared by one of a number of known routes. For example, where $R_3M$ is $(CH_3)_3Ga$ or $(CH_3)_3In$, $GaCl_3$ or $InCl_3$ may be caused to react with either $CH_3Li$ or with a suitable Grignard reagent in the presence of the ether E in the form of a solvent.

According to a second aspect of the present invention there is provided an adduct of general formula $(R_3M)_y.L$ wherein $R_3$ represents three alkyl groups R which may be the same or different, M represents a Group III metallic element, L represents an aryl containing Group V donor ligand provided by an organic Lewis base which is stable at 20° C., and y is an integer equal to the number of Group V donor atoms present in the ligand. L preferably represents a phosphorus donor ligand. M preferably represents aluminium, gallium or indium. Each R preferably represents a lower alkyl group, most preferably methyl.

The Lewis base from which the ligand L is provided is preferably a low volatility solid melting in the range 50° C. to 200° C.

The adduct $(R_3M)y.L$ preferably has a heat of formation between 5 and 15 kcal $mol^{-1}$ most preferably from 6 to 12 kcal $mol^{-1}$.

L is conveniently derived from a Lewis base in which the Group V donor atom present in the base is trivalent and is bonded directly to at least one adjacent aryl groups.

L is preferably of general formula I

and is most preferably of general formula II

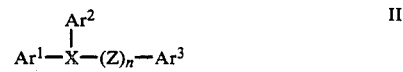

wherein $Ar^1$, $Ar^2$ and $Ar^3$ are the same or different and are aryl groups, X is a Group V atom, Y is an aryl or aryl-containing group, Z is

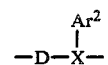

wherein D is an aromatic or aliphatic group and $Ar^4$ is an aryl group, and n is an integer from 1 to 5. Preferably X is phosphorous.

Each of the groups $Ar^1$, $Ar^2$ and (in Formula II) $Ar^3$ and $Ar^4$ may be selected from phenyl, substituted phenyl (eg o-, p-, or m-tolyl $C_6H_4CH_3$, or mesityl $C_6H_2(CH_3)_3$), p-diphenyl or naphthyl. Preferably, the groups $Ar_1$, $Ar_2$, $Ar_3$ and $Ar_4$ are phenyl.

D is preferably an aliphatic chain $(CH_2)_m$ where m is an integer from 1 to 12, most preferably from 2 to 4, and n is preferably from 1 to 3.

Examples of monodentate ligands L of general formula I are triphenylphosphine, tris-p-tolylphosphine, trimesitylphosphine, tris-p-biphenylphosphine and tri-naphthylphosphine. Examples of bi- and poly-dentate ligands L of general formula II are DIPHOS($Ph_2PCH_2CH_2PPh_2$), TRIPHOS($Ph_2PCH_2CH_2P(Ph)CH_2CH_2PPh_2$) and TETRAPHOS-1($Ph_2PCH_2CH_2P(Ph)CH_2CH_2P(Ph)CH_2CH_2PPh_2$).

By producing metal alkyls by the method according to the first aspect of the present invention it is possible to avoid the difficulties mentioned above in relation to manufacture, transportation and handling of the volatile metal alkyl. However, in order to make the metal alkyl available at the point of use (eg in a VPE apparatus) it may be separated from the adduct of formula $(R_3M)_y.L$ by heating the adduct to a relatively low temperature, eg either under an inert gas at atmospheric pressure or under reduced pressure. For example, trimethyl gallium may be obtained from $(CH_3)_3Ga.PPh_3$ by heating this adduct to 180° C. under nitrogen at atmospheric pressure or to 90° C. under reduced pressure ($10^{-2}$ mmHg).

Adducts of formula $(R_3M)_y.L$ embodying the second aspect of the present invention are preferred to known adducts containing ligands such as $(CH_3)_3P$ and to adducts containing ethers and other oxygen containing ligands for use in methods for the production of semiconductor compounds because the ligand L may be readily separated from the alkyl and traces of the ligand L are less likely to act as a dopant in the semiconductor compounds produced.

Embodiments of the present invention will now be described by way of example with reference to the accompanying drawings, in which.

Figure 1:
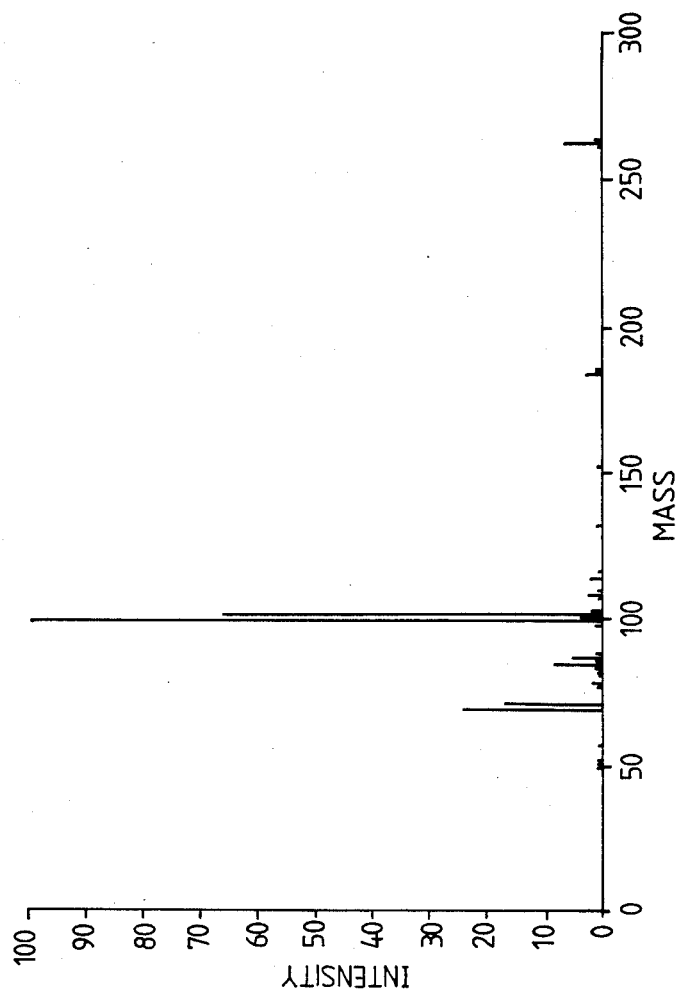
FIG. 1 is a graph of intensity versus atomic mass being a mass spectrum of the product of Reaction 2 specified below.

In the following example the following symbols are used:

m.p.=melting point
b.p.=boiling point
NMR=nuclear magnetic resonance spectrum
IR=infra-red
ppm=parts per million

EXAMPLE 1

Trimethyl gallium $Me_3Ga$ was produced from the adduct $Me_3Ga.PPh_3$ by obtaining the adduct from the precursor adduct $Me_3Ga.Et_2O$, where Et=ethyl. The precursor adduct was obtained from methyl lithium in diethyl ether. The overall reaction sequence which was used is as follows:

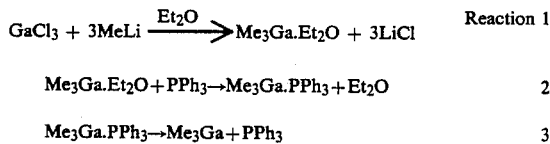

$Me_3Ga.Et_2O + PPh_3 \rightarrow Me_3Ga.PPh_3 + Et_2O$     2

$Me_3Ga.PPh_3 \rightarrow Me_3Ga + PPh_3$    3

1.1 Preparation of trimethyl gallium etherate: Reaction 1

Methyllithium in ether (1.67M solution, 112 ml) was added to $GaCl_3$ (11.0 g in either 50 ml) with ice cooling and stirring. The mixture was stirred over-night at room temperature, filtered and the filtrate fractionated on a Vigreux column (16 cm long) until all solvent was removed and the $Me_3Ga.Et_2O$ distilled off (b.p. 99° C.). The yield was 10.3 g (87%).

1.2 Preparation of the adduct $Me_3Ga.PPh_3$: Reaction 2

Triphenylphosphine (3.6 g) in benzene (30 ml) was added to $Me_3Ga.Et_2O$, 92.6 g) in benzene (10 ml) at room temperature. The mixture was fractionated on the Vigreux column (16 cm long), taking off the low boiling fraction (36° C.) until the temperature of the distillate reached 80° C. (b.p. of benzene). The mixture was then cooled down and concentrated by evaporation of the solvent under reduced pressure up to the point of crystallisation, 1.7 g of which crystalline compound was obtained. This was recrystallized from pentane (about 120 ml) until it had a constant melting point. The compound melts without significant decomposition at 132° C. IR, NMR and mass spectra were obtained to confirm the structure of the adduct. A sample was also the subject of microanalysis (C and H): the results obtained were: Found: C, 66.6% H, 6.47%; $Me_3Ga.PPh_3$ requires: C, 66.9%, H, 6.41%.

The IR, NMR and mass spectra results obtained are as follows:

$^1H$ NMR (in $C_6D_6$): The molar ratio of the hydrogen atoms in $PPh_3$ phenyl groups (δ, 8.25–6.90 ppm) to hydrogen atoms in $Me_3Ga$ methyl groups (δ, 0.2 ppm) was found by the integration of the NMR peaks=1.8:1 (calculated 1.66:1). The slightly high value obtained is explained as due to traces of $C_6H_xD_{6-x}$ (x=1 to 6) species in the $C_6D_6$ solvent which contributes to the intensity of the phenyl peaks.

Mass spectrum (70 eV): The results are illustrated in FIG. 1. No parent ion for the adduct was found. Found: $PPh_3^+$ mass 262.3 $Me_3Ga^+$ mass 116.2 and 114.2 (due to $^{71}Ga$ and $^{69}Ga$ isotopes); $Me_3Ga^+$ mass 101.2 and 99.3; $MeGa^+$ mass 86.2 and 84.1; $Ga^+$ mass 71.1 and 69.1.

The ratio of the intensities of the gallium containing species for the two isotopes of gallium (71 and 69) is approximately 1.5, which is in good agreement with the ratio of natural abundance of the isotopes $Ga^{69}$—60.4% and $Ga^{71}$—39.6%.

Figure 2:
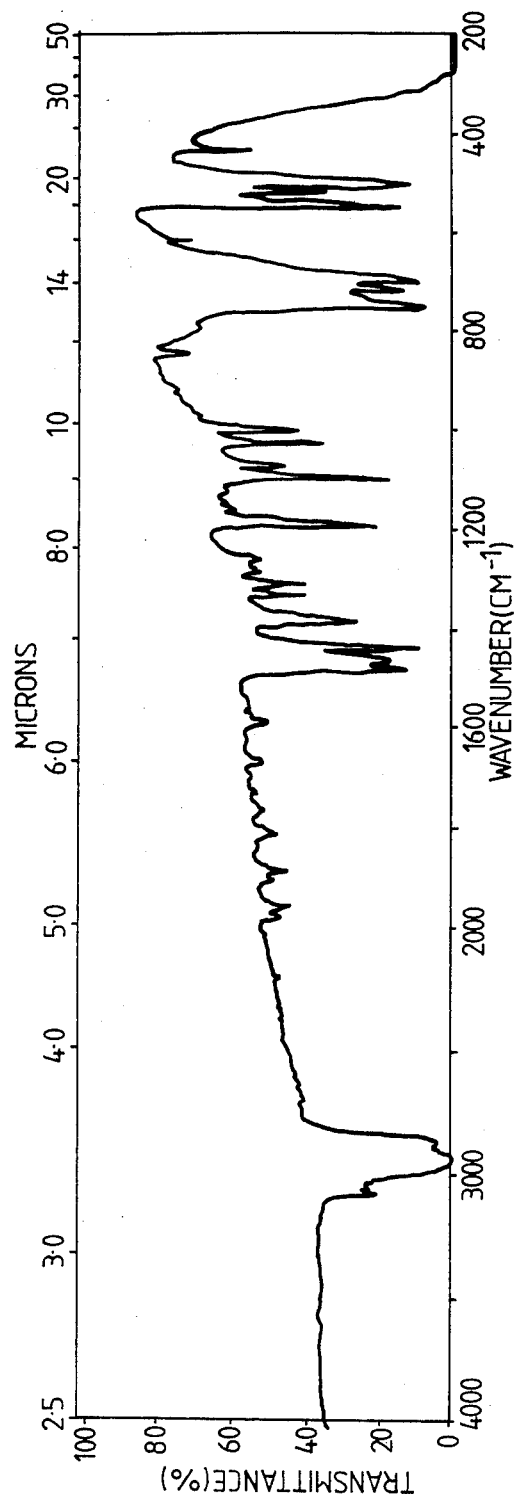
FIG. 2 is a graph of infra-red transmittance versus wave number being an infra-red absorption spectrum of the product of Reaction 2 specified below.

IR spectrum: The spectrum obtained is shown in FIG. 2. This assists in the confirmation of the constitution of the adduct.

1.3 Preparation of $Me_3Ga$: Reaction 3

The preparation of the $Me_3Ga.PPh_3$ was repeated twice for the purpose of splitting the adduct into $Me_3Ga$ and $PPh_3$ by the action of heat using an oil bath:
1. under nitrogen at atmospheric pressure, and
2. under reduced pressure.

Excess $PPh_3$ (ca. 20%) was used each time. The adduct was obtained as in 1.2 above except that at the end instead of crystallisation from benzene the solvent was evaporated under reduced pressure and the product was used without further purification.

The sample heated under nitrogen started showing slow evolution of a gas, identified as $Me_3Ga$ at 180° C. The heating was stopped at this point.

The sample heated under reduced pressure ($10^{-2}$ mm Hg) started evolving $Me_3Ga$ at about 80° C. (temperature of the oil bath). At that temperature the solid in the flask started melting (m.p. of $PPh_3$=80° C.). The heating was continued, slowly raising the temperature to 90° C. The heating was stopped approximately 15 mins after all the contents of the flask had melted and no more evolution of the gas was visible. The $Me_3Ga$ was collected in a liquid nitrogen trap.

The $Me_3Ga$ was identified by its NMR spectrum (δ, −0.07 ppm; $C_6D_6$); 1.3 g of $Me_3Ga$ was collected giving the yield 71% based on $Me_3Ga.Et_2O$. (The preparation was started from 3 g of $Me_3Ga.Et_2O$).

The residue left in the flask after heating was tested by NMR. It showed only a negligible amount of methyl gallium species in form of the adduct, the bulk being $PPh_3$ which could thus be recycled in the process.

EXAMPLE 2

Preparation of $Me_3In$ from the adduct
$(Me_3In)_2.DIPHOS$ where
$DIPHOS = Ph_2P-CH_2-CH_2-PPh_2$, where
Ph=phenyl Step 2a: Preparation of the adduct $(Me_3In)_2DIPHOS$
Methyl lithium, 1.3 molar solution in ether (65 ml) was added to $InCl_3$ (6 g) in ether (50 ml). The mixture was refluxed for 2 h and filtered. Benzene (100 ml) was added to the filtrate by the DIPHOS (6 g) solution in benzene (100 ml). The ether was removed by fractional distillation on a Vigreux column. The remaining benzene solution was filtered and the solvent was evaporated under reduced pressure. The crude compound (9.78 g) m.p. 156° C. was purified by repeated crystallisation from benzene up to the constant melting point (163° C.). The compound was characterised by IR, NMR, mass spectrum and elemental analysis.

The results were as follows:

NMR. $^1$H chemical shifts (ppm)

In(CH$_3$)$_3$: 0.07; DIPHOS: CH$_2$: 2.50 (doublet) C$_6$H$_5$: 7.52–7.27 and 7.07–6.9; from the integration the ratio CH$_3$:CH$_2$ was found to be 4.5:1 as expected.

Elemental analysis: Found: C, 53.83; H, 5.90%. Calculated for (Me$_3$In)$_2$.DIPHOS: C, 53.51; H, 5.89%.

| Mass spectrum | Mass | Intensity |
|---|---|---|
| DIPHOS$^+$ | 397.8 | 1.4% |
| In$^{115}$Me$_2$$^+$ | 144.9 | 100 |
| In$^{113}$Me$_2$$^+$ | 143.0 | 4.7 |
| In$^{115}$Me$^+$ | 130.0 | 12.2 |
| In$^{113}$Me$^+$ | 128.0 | 1.3 |

Step 2b: Preparation of Me$_3$In from the (Me$_3$In)$_2$DIPHOS adduct (Me$_3$In)$_2$.DIPHOS (3.07 g) was heated under reduced pressure (10$^{-2}$ mmHg) in a flask connected to a glass container immersed in liquid nitrogen and joined to a vacuum pump. The heating (oil bath) was increased gradually. At approximately 80° C. the Me$_3$In started collecting in the glass container. At 120° C. the dissociation reaction became vigorous and the contents of the reaction flask turned light brown and frothy. The temperature was raised slowly to 130° C. and kept constant until all bubbling ceased. The white compound collected in the glass container (1.01 g) was identified by NMR as Me$_3$In (one peak at 0.2 ppm), yield 87%. The residue left in the reaction flask gave an NMR spectrum showing DIPHOS peaks only.

EXAMPLE 3

Preparation of Me$_3$Ga from the adduct (Me$_3$Ga)$_2$.DIPHOS

Step 3a: Preparation of the adduct (Me$_3$Ga)$_2$.DIPHOS

Me$_3$Ga.Et$_2$O was prepared as in Example 1 from GaCl$_3$ and MeLi in ether and distilled before use. DIPHOS (8.2 g) solution in benzene (150 ml) was added to Me$_3$Ga.Et$_2$O (6.8 g) in benzene (50 ml) and the mixture was stirred for half an hour at room temperature. The more volatile ether was then removed by fractional distillation (Vigreux column) and the benzene evaporated under reduced pressure. The crude compound (12.5 g) mp. 155° C. was purified by repeated crystallisation from benzene up to the constant melting point (163° C.).

The compound was characterised by NMR, IR, mass spectrum and elemental analysis.

NMR. $^1$H chemical shifts (ppm): Ga(CH$_3$)$_3$:0.15; DIPHOS:CH$_2$, 2.52; C$_6$H$_5$ 7.55–7.27 and 7.1–6.87.

Elemental analysis: Found: C, 61.39; H, 6.73%. Calculated for (Me$_3$Ga)$_2$.DIPHOS: C, 61.20; H, 6.74%.

Step 3b: Preparation of Me$_3$Ga from the (Me$_3$Ga)$_2$.DIPHOS adduct (Me$_3$Ga)$_2$.DIPHOS (3.32 g) was heated under reduced pressure (10$^{-2}$ mmHg) in a flask jointed to a glass receiver immersed in liquid nitrogen and connected to a vacuum pump. The temperature of the oil bath was slowly raised to 130° C. The evolution of Me$_3$Ga started at about 80° C. and became vigorous at 110° C. The collected dry Me$_3$Ga was redistilled under reduced pressure at room temperature and identified by NMR (one peak at 0.12 ppm). Yield 1.01 g (91.2%).

The residue left in the reaction flask gave an NMR spectrum showing 'DIPHOS' peaks only.

EXAMPLE 4

Preparation of (CH$_3$)$_6$Al$_2$ from the adduct (Me$_3$Al)$_2$.DIPHOS

Step 4a: Preparation of the adduct (Me$_3$Al)$_2$.DIPHOS

"Trimethyl aluminium" was added, in the form of 21 ml of a solution (1.15 Molar) of Me$_6$Al$_2$ in hexane, to DIPHOS (10.2 g) dissolved in benzene (250 ml). About 50 ml of volatile material was distilled over, using a fractionating column and the remaining solution was concentrated to 50 ml under reduced pressure. A white solid was deposited and this was filtered off. Yield 9.2 g (62%), Mp. ~163° C.

NMR. $^1$H chemical shifts (ppm): Al(CH$_3$)$_3$: −0.175; DIPHOS, CH$_2$: 2.62, C$_6$H$_5$: 6.87 to 7.12 and 7.32 to 7.61. Integration: CH$_3$:CH$_2$=4.5:1.

Mass Spectrum: Major peaks were given by DIPHOS$^+$ (m/z, 398.4, 68.1%) and Me$_2$Al$^+$ (m/z, 57.3, 100%).

Step 4b: Preparation Me$_6$Al$_2$ from the (Me$_3$Al)$_2$.DIPHOS adduct (Me$_3$Al).DIPHOS (3.0 g) was heated under reduced pressure and the volatile Me$_6$Al$_2$ was collected in a cold trap (liquid N$_2$ temp.). The dissociation began at approx. 115° C. (heating bath temp.) At 140° C. the material melted and bubbling was observed. Heating was continued until bubbling ceased. Yield 0.71 g (87.6%).

The product was identified as Me$_6$Al$_2$ By its $^1$H NMR spectrum ($\delta$, −0.35 ppm).

EXAMPLE 5

Preparation of Me$_3$In from the adduct (Me$_3$In)$_3$.TRIPHOS

Step 5a: Preparation of the adduct (Me$_3$In)$_3$.TRIPHOS.

TRIPHOS (1.5 g) was dissolved in benzene (20 ml) and Me$_3$In (1.3 g) was added by condensation at liquid nitrogen temperature under reduced pressure. After warming to room temperature the solvent was evaporated under reduced pressure leaving an oil (2.8 g).

NMR. $^1$H chemical shifts (ppm): In(CH$_3$)$_3$: 0.125; TRIPHOS, CH$_2$: 1.90–2.60, C$_6$H$_5$: 6.9–7.17 and 7.27–7.67. Integration: CH$_3$:CH$_2$=3.10:1.

Mass Spectrum: Major peaks appeared at m/z 540 (TRIPHOS), 145/143 (Me$_2$In) and 130/128 (MeIn).

Step 5b: Preparation of Me$_3$In from the (Me$_3$In)$_3$.TRIPHOS adduct.

(Me$_3$In)$_3$.TRIPHOS (2.8 g) was heated under reduced pressure and the Me$_3$In was collected by condensation in a cold trap at the temperature of liquid nitrogen. Release of Me$_3$In from the adduct was initially observed with the heating bath at 60° C. and became rapid at 75° C. The temperature was slowly raised to 145° C. and over a period of 3 hours a quantity of Me$_3$In (1.0 g, 75.7% yield) was collected and identified by $^1$H NMR. An NMR spectrum on the non-volatile residue confirmed that it was TRIPHOS containing a small amount of coordinated Me$_3$In.

EXAMPLE 6

Preparation of Me$_6$Al$_2$ from the adduct (Me$_3$Al)$_4$.TETRAPHOS

Step 6a: Preparation of the adduct (Me$_3$Al)$_4$.TETRAPHOS.

TETRAPHOS (2.55 g) was suspended in benzene (100 ml) and to it was added Me$_6$Al$_2$ in the form of a solution (6.6 ml) in hexane (1.15 Molar in Me$_6$Al$_2$). The TETRAPHOS then dissolved by reaction with Me$_6$Al$_2$ giving a soluble adduct. Hexane and other volatile impurities were removed by fractional distillation and evaporation of the benzene at room temperature under reduced pressure left a white solid adduct (3.92 g).

NMR. $^1$H chemical shifts (ppm): Al(CH$_3$)$_3$: −0.25; TETRAPHOS, CH$_2$: 1.85–2.62, C$_6$H$_5$: 6.87–7.15 and 7.30–7.75. Integration: CH$_3$:CH$_2$=3:1.

Step 6b: Preparation of Me$_6$Al$_2$ from the (Me$_3$Al)$_4$.TETRAPHOS adduct (Me$_3$Al)$_4$.TETRAPHOS (1.58 g) was heated under reduced pressure and the Me$_6$Al$_2$ was collected by condensation in a liquid nitrogen cold trap. Release of Me$_6$Al$_2$ was observed when the batch temperature reached 60° C. and the temperature was slowly raised to 140° C. The yield of Me$_6$Al$_2$ (0.48 g) was quantitative.

We claim:

1. A method of preparing a Group III metal alkyl which comprises (a) combining a metal alkyl with a ligand to form an adduct of said alkyl with said ligand and (b) heating the adduct to provide thermal dissociation thereof thereby releasing the Group III metal alkyl as a gaseous product, characterized in that the adduct formed is of formula (R$_3$M)$_y$.L wherein R$_3$ represents three alkyl groups R which may be the same or different, M represents a Group III metallic element, L represents an aryl-containing Group V donor ligand provided by an organic Lewis base which is stable at 20° C. and y is an integer equal to or less than the number of Group V donor atoms present in the ligand.

2. A method according to claim 1 characterised in that L is an aryl-containing phosphorus donor ligand.

3. A method according to claim 1 or claim 2 characterised in that the organic Lewis base has a melting point of from 50° C. to 200° C.

4. A method according to claim 1 characterised in that the heat of formation of the adduct is between 5 and 15 kcal mol$^{-1}$.

5. A method according to claim 4 characterised in that the heat of formation of the adduct is from 6 to 12 kcal mol$^{-1}$.

6. A method according to claim 1 characterised in that the Lewis base for providing the ligand L is selected from aryl-containing Group V Lewis bases in which each group V donor atom present in the base is trivalent and is bonded directly to at least one adjacent aryl group.

7. A method according to claim 6 characterised in that the organic Lewis base and the ligand L are both of general formula I $$Ar^1-\underset{\underset{Ar^2}{|}}{X}-Y \qquad \text{I}$$

wherein
Ar$^1$ and Ar$^2$ are the same or different and are aryl groups,
X is a Group V atom, and
Y is an aryl or aryl-containing group.

8. A method according to claim 7 characterised in that the organic Lewis base and the ligand L are both of general formula II $$Ar^1-\underset{\underset{Ar^2}{|}}{X}-(Z)_n-Ar^3 \qquad \text{II}$$

wherein
Ar$^1$, Ar$^2$ and X are as defined in claim 7, Ar$^3$ is an aryl group which may be the same or different to one or both of Ar$^1$ and Ar$^2$,
Z is $$-\underset{\underset{Ar^4}{|}}{D}-X-$$

wherein D is an aromatic or aliphatic group and Ar$^4$ is an aryl group, and
n is an integer from 1 to 5.

9. A method according to claim 8 characterised in Ar$^1$, Ar$^2$, Ar$^3$ and Ar$^4$ are independently selected from phenyl, substituted phenyl, p-diphenyl and naphthyl.

10. A method according to claim 9 characterised in that Ar$^1$, Ar$^2$, Ar$^3$ and Ar$^4$ are each phenyl.

11. A method according to claim 8 characterised in that D is an aliphatic chain of formula (CH$_2$)$_m$ where m is an integer from 1 to 12.

12. A method according to claim 11 characterised in that m is from 2 to 4.

13. A method according to claim 8 characterised in that n is from 1 to 3.

* * * * *